United States Patent
Broad, Jr.

[11] Patent Number: 5,477,865
[45] Date of Patent: Dec. 26, 1995

[54] INVERTED RESERVOIR CONDOM

[76] Inventor: Robert L. Broad, Jr., 2300 Brookwood Dr., SE., Decatur, Ala. 35601

[21] Appl. No.: 977,919

[22] Filed: Nov. 18, 1992

Related U.S. Application Data

[63] Continuation-in-part of Ser. No. 614,154, Nov. 16, 1990, Pat. No. 5,165,422, and Ser. No. 300,140, Jan. 23, 1989, Pat. No. 4,972,850, and Ser. No. 300,139, Jan. 23, 1989, Pat. No. 4,987,905.

[51] Int. Cl.[6] .................................................. A61F 6/00
[52] U.S. Cl. ........................ 128/344; 128/842; 128/918
[58] Field of Search .................................. 128/842, 844, 128/918, 397, 398, 399, 350, 351, 352, 347, 352, 857–860

[56] References Cited

U.S. PATENT DOCUMENTS

| | | | |
|---|---|---|---|
| 4,872,063 | 10/1989 | Nishizono | 128/844 |
| 4,945,923 | 8/1990 | Evans et al. | 128/844 X |
| 5,065,771 | 11/1991 | Ferguson | 128/835 |

FOREIGN PATENT DOCUMENTS

| | | |
|---|---|---|
| 0111720 | 2/1928 | Germany. |
| 2410697 | 6/1974 | Germany. |

*Primary Examiner*—Sam Rimell

[57] ABSTRACT

A condom having an elongated tubular configuration with an open end and a closed end. The closed end of the condom is provided with a reservoir which is positioned inside the condom and which has a free end extending toward the open end of the condom. Preferably, the condom has a pair of strips rolled into the condom on opposite sides thereof with the strips having free ends extending away from each other and with intermediate portions of the strips being temporarily bonded to each other to provide slack in the strips.

15 Claims, 3 Drawing Sheets

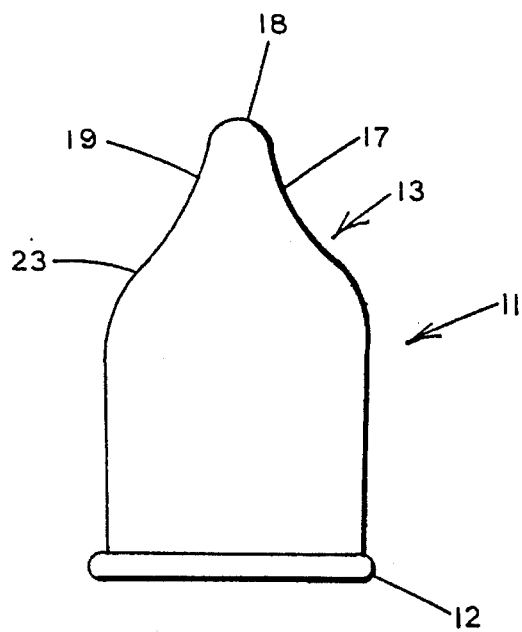
FIG. 1
PRIOR ART
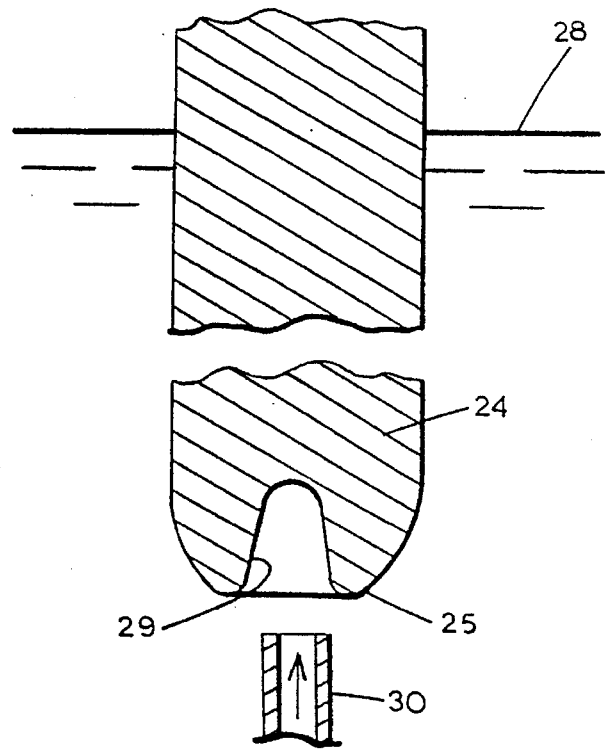
FIG. 2
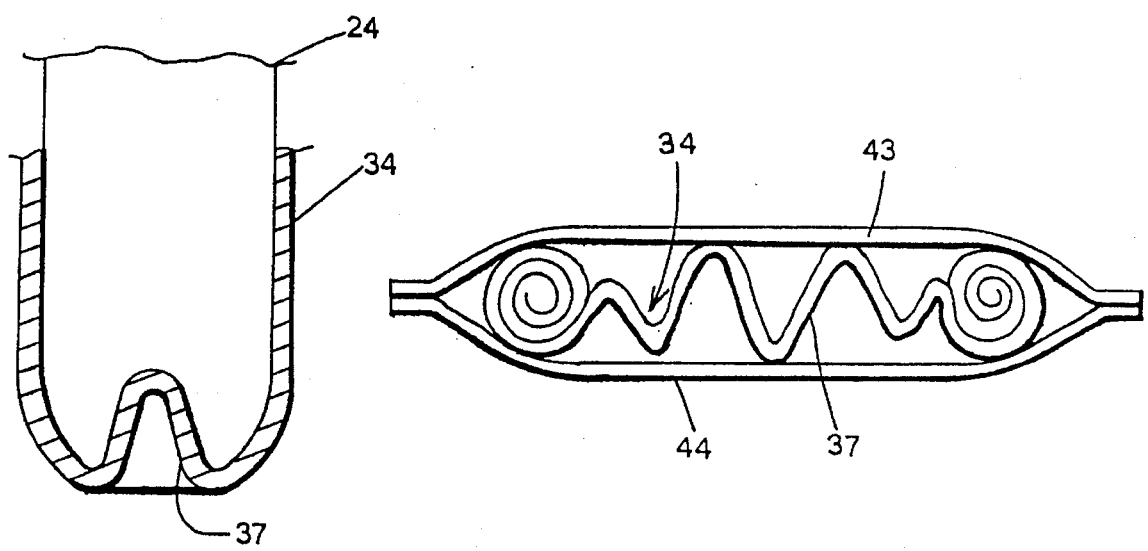
FIG. 3
FIG. 4

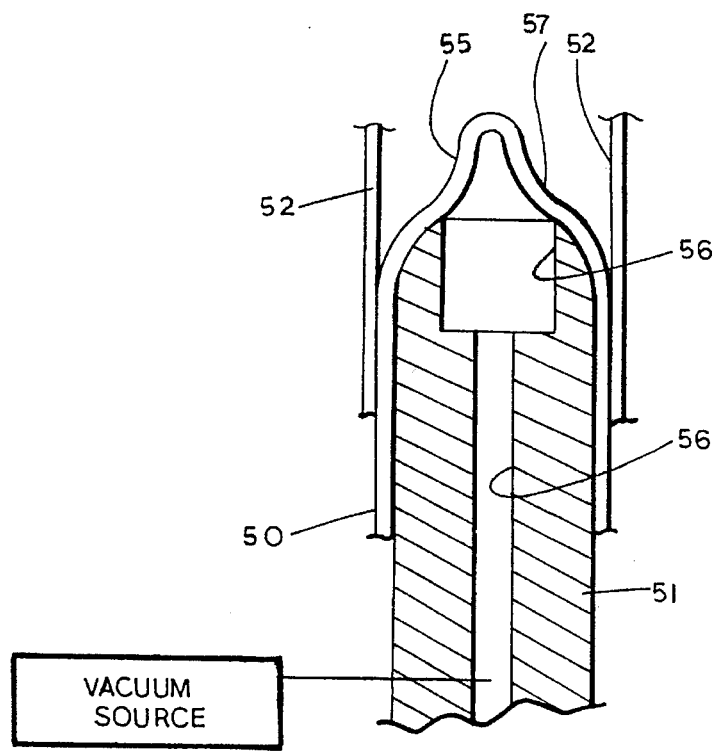
FIG. 8
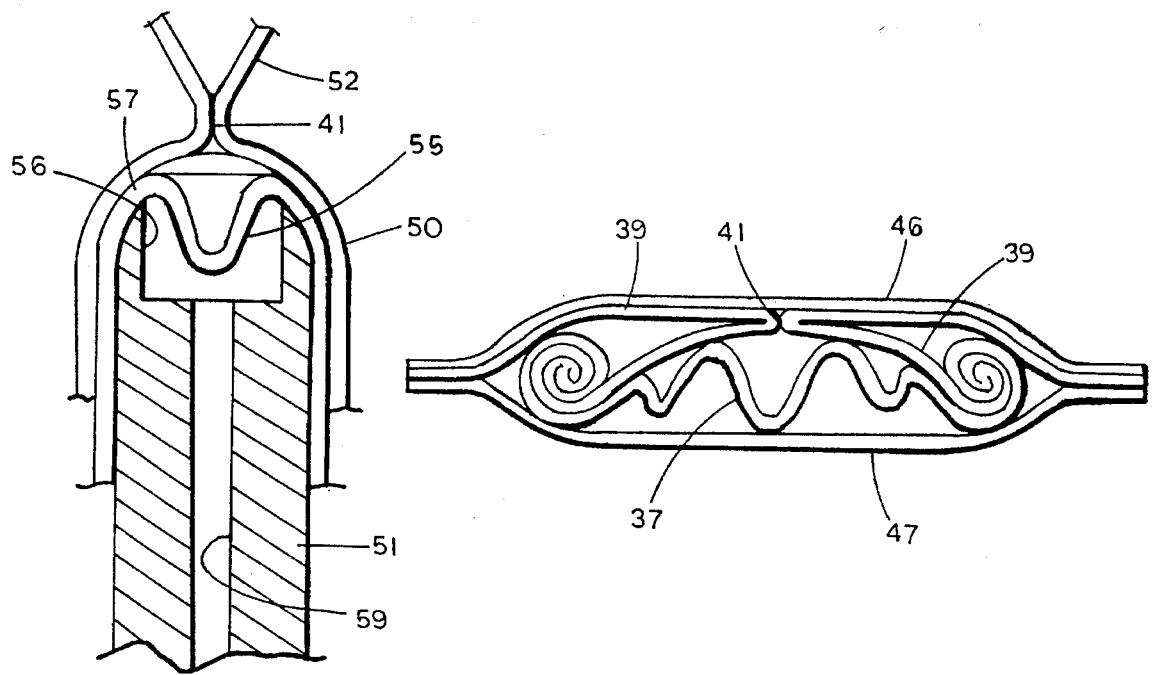
FIG. 9
FIG. 10

5,477,865

INVERTED RESERVOIR CONDOM

This is a continuation-in-part application of application Ser. No. 07/614,154, filed Nov. 16, 1990 for "APPARATUS FOR ASSEMBLING A CONTRACEPTIVE DEVICE" now U.S. Pat. No. 5,165,422; Ser. No. 07/300,140, filed Jan. 23, 1989 for "NO HANDS CONTRACEPTIVE DEVICE" (now U.S. Pat. No. 4,972,850); and Ser. No. 07/300,139 filed Jan. 23, 1989 for "NO HANDS CONTRACEPTIVE DEVICE" (now U.S. Pat. No. 4,987,905).

FIELD OF THE INVENTION

This invention relates to condoms and methods of making the same.

PRIOR ART

Conventional condoms have been known for decades. During this time little or nothing has been done to alleviate the well known problems associated with the use of condoms. Conventional condoms are difficult to put on such that donning a conventional condom requires an excessive amount of time. This is borne out by the results of a recent survey of several thousand people done by a well known consumer magazine. This survey showed that approximately 70% of those surveyed, both men and women, complained that condoms "interrupt lovemaking", meaning that condoms take too long to put on. This and other problems have existed with condoms for decades.

The difficulty of donning a condom is increased by the requirement, spelled out in the instructions on every package of reservoir type condoms, that the user squeeze the condom reservoir flat and hold it that way while the condom is being donned. The invention disclosed and claimed herein solves this problem automatically without the user having to touch the reservoir of the condom.

SUMMARY OF THE INVENTION

A condom having an inverted reservoir is made by dipping the lower end or an elongated cylindrical form into a latex solution to coat the form with the solution. The form has in the lower end thereof a cavity the surface of which is coated by a submerged spray as the form passes through the latex solution. The coated form is withdrawn from the latex solution and the coating is then cured in a known manner to form the condom. This condom has an inverted reservoir which is and remains collapsed when the condom is donned, thereby eliminating the necessity of holding the reservoir in a collapsed condition as the condom is put on. Preferably, the condom will have a pair of strips rolled into it on opposite sides thereof for unrolling the condom onto the penis, with the free ends of the strips extending away from the condom in opposite directions and intermediate portions of the strips being bonded to each other in a temporary bond.

DESCRIPTION OF THE DRAWINGS

FIG. 1 is a side view of a conventional prior art condom showing its configuration.

FIG. 2 is a fragmentary cross sectional view of a form on which the condom of this invention can be made.

FIG. 3 is a cross sectional view showing the completed condom on the form of FIG. 2.

FIG. 4 is an enlarged cross sectional view of the condom of this invention inside a package, with hatching being omitted for clarity.

FIG. 5 is a plan view showing the configuration of the condom as it is in position to be donned.

FIG. 6 is a cross sectional view of the structure of FIG. 5 after the condom has been donned, showing how the reservoir of the condom remains collapsed after the condom has been put on.

FIG. 8 is a fragmentary cross sectional view showing a condom mounted on a form which is used to invert the reservoir of a conventional condom to allow the strips of FIG. 7 to be bonded together as close as practical to the main body of the condom and to obtain the advantages of an inverted reservoir described below.

FIG. 9 is a view of the structure shown in FIG. 8 after the reservoir of the condom has been inverted and intermediate portions of the pair of strips to be used for unrolling the condom have been bonded together.

FIG. 10 is an enlarged cross sectional view of the condom of FIG. 9 in a package, with hatching being omitted for clarity.

DETAILED DESCRIPTION OF THE INVENTION

Figures 5, 6:
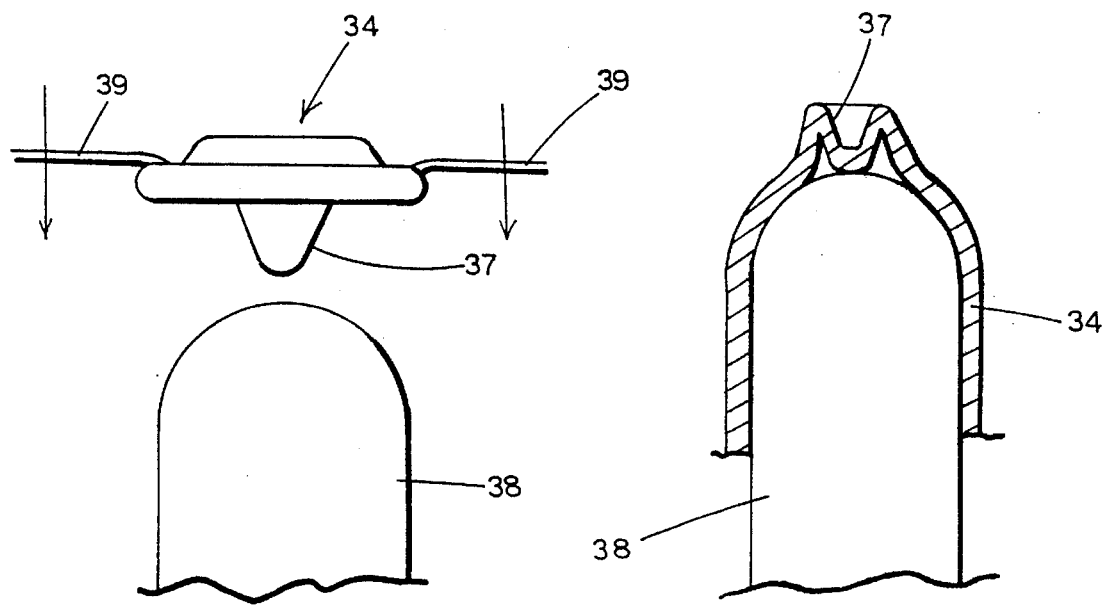

Referring now in detail to the drawings, there is shown in FIG. 1 a conventional prior art condom 11 having an open end 12 and a closed end 13, with a reservoir 17 being provided on the closed end of the condom. The reservoir 17 includes a rounded end 18 and a generally cylindrical portion 19, with the generally cylindrical portion 19 having a slight taper. A generally frustoconical portion 23 interconnects the main body of the condom and the reservoir 17.

In FIG. 2 there is shown a form 24 on which the condom of this invention can be made. The form 24 is in the form of an elongated cylinder having a rounded free lower end 25 which is to be dipped into a latex solution 28 for forming a condom. The free end 25 of the form 24 is provided with a recess 29 having the configuration shown in FIG. 2. When this free end is dipped into the latex solution 28 the recess 29 will trap air so that the surface of this recess would not normally be coated with the latex solution. This problem is solved by providing submerged fountains or jets 30 (FIG. 2) which spray the latex solution into the recess 29 to coat its surface as the form passes over the jets. The latex solution on this surface will be the inverted reservoir of the condom after the latex is cured.

When the form is removed from the latex solution and the coating on the form is cured, the result is a condom 34 with an open end and a closed end having an inverted reservoir 37. By the term "inverted" it is meant that the reservoir 37 is inside the remainder of the condom 34 and the free end of the reservoir extends or points toward the open end of the condom. This is contrasted with the conventional condom 11 of FIG. 1, where the reservoir 17 is outside the remainder of the condom and extends or points away from the open end 12 of the condom. The purpose of this inverted reservoir is to cause the reservoir 37 to be collapsed and empty of air without the user having to touch it as he puts the condom on.

FIG. 4 shows the condom positioned in a package made up of a pair of packaging sheets 43 and 44 secured to each other around the edges thereof to form a package for the condom 34. From this it can be seen that when the package is opened and the condom unrolled, the reservoir 37 will be inside the remainder of the condom and its free end will extend or point toward the open end of the condom.

FIG. 5 shows the condom as it is about to be put on. In this view, a pair of strips 39 each having one end rolled into the condom are used to unroll the condom onto the penis 38. The user opens the package by tearing it into two parts. Without releasing the two parts of the package, the user moves the parts away from each other to pull the condom out of the package. He then, still holding the two parts of the package, moves the condom 34 into contact with the end of the penis 38 and then pulls the strips 39 to unroll the condom onto the penis. With a quick flick of the wrists, this condom can be put on in a split second without the user ever touching it.

It is not necessary that the strips 39 be used, since the inverted reservoir 37 will be collapsed after the condom has been put on regardless of whether the strips 39 are used. However, the use of the strips 39 makes the condom much easier and faster to put on.

As the condom 34 is brought toward the penis 38 (FIG. 5) the penis 38 first contacts the end of the inverted reservoir 37 and then the rolled condom. Contact of the penis 38 with the condom seals the condom so that no more air can enter it. This forces the inverted reservoir to remain in an inverted configuration as the condom is unrolled onto the penis.

FIG. 6 shows the condom after it has been put on. The inverted reservoir 37 is essentially empty of air as it would be if the user squeezed it flat and held it that way while putting the condom on. If one pulls the inverted reservoir 37 away from contact with the end of the penis 38 and then releases it, it will either return to the configuration shown in FIG. 6 or it will flatten as though it was being squeezed between thumb and forefinger. Thus, the reservoir is emptied of air without the user having to touch it.

To avoid having the package interfere with the donning of the condom when the strips are used it is necessary to have the condom substantially out of the two parts of the package before it is put on. This can be done simply by moving the two parts of the package away from each other such that the strips pull the condom out of the two parts of the package. However, it is critical that this be done without any premature unrolling of the condom. If the condom unrolls even a slight amount before it is in contact with the penis it is likely to tangle to the point where it must be discarded. This problem is discussed in more detail in U.S. Pat. Nos. 4,972,850 and 4,987,905.

Figure 7:
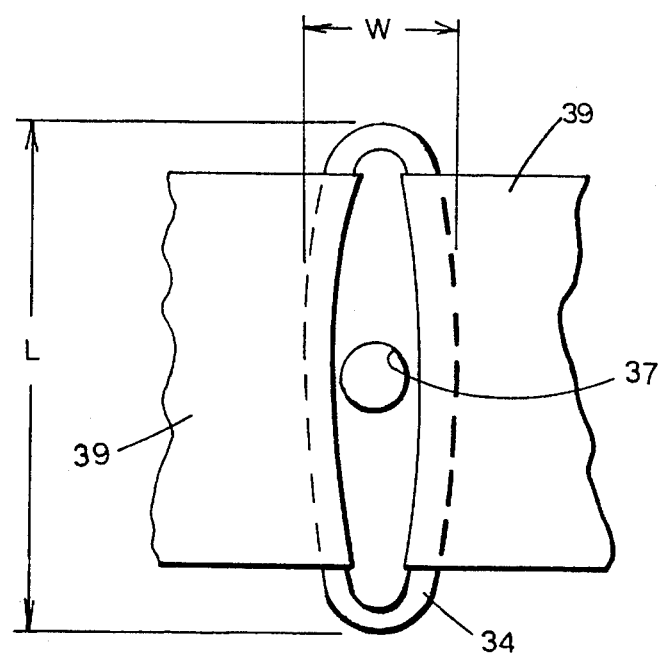
FIG. 7 is a plan view of a condom having a pair of strips rolled into it on opposite sides thereof, showing the elliptical configuration which strips of the preferred width, when rolled into the condom, cause the rolled condom to assume.

If the strips 39 are used, they should have a minimum width to prevent premature unrolling of the rolled condom. The widths of the strips 39 should be sufficiently great to cause the rolled condom 34 to assume an elliptical configuration having a length (L) to width (W) ratio of at least 1.2, as illustrated in FIG. 7. For some reason this prevents premature unrolling of the condom and the attendant tangling. The minimum width of the strips 39 can also be characterized in terms of the length of the circumference of the rolled condom. The sum of the widths of the strips, at their widest part, should be at least 20%, preferably 30%, of the length of the circumference of the rolled condom.

The thickness of the strips may be from about 0.3 mils to about 2.0 mils and the strips can be cut from a polyethylene film such as that used for trash bags. Thinner strips are more difficult to handle while thicker strips are more difficult to roll. Both the strip width and thickness will have an affect on the condom's configuration and thereby its resistance to premature unrolling, as clearly shown in FIG. 12 of U.S. Pat. No. 4,972,850. One selects a workable thickness and then uses a width sufficient to cause the rolled condom to assume the configuration described above.

To avoid premature unrolling of the condom as it is pulled out of the package, in addition to providing a minimum strip width, the strips are provided with sufficient slack that there will be no unrolling of the condom at this point. A preferred way to insure that there is sufficient slack in the strips is to bring intermediate portions of the strips together and adhere them to each other in a temporary bond which maintains the slack in the strips during further processing and packaging.

FIG. 10 shows the condom 34, with the strips 39, in a package made up of a pair of packaging sheets 46 and 47 of a known type sealed to each other around the edges thereof. One end of each of the strips 39 is rolled into the condom 34 and the other end is secured to the opposite sealed edges of the package. Intermediate portions of the strips 39 are brought together and spot bonded to each other. By "spot bonded" is meant that the strips 39 are secured to each other in a temporary bond which has sufficient strength to hold the strips 39 together during further processing but which is weaker than the strip itself. With such a bond, when an increasing tension is applied to the strips 39 the bond will break and allow the strips to separate (and thereby provide slack) before sufficient tension is applied to break one of the strips. The location of the spot bond is indicated by reference numeral 41 in FIG. 10.

The spot bonding is preferably done by fusing portions of the strips 39 together. For example, the spot bonding may be achieved by holding the thermoplastic strips 39 in contact with each other and piercing them with a heated pin (not shown). Touching the strips 39 with the tip of a hot soldering gun (not shown) while the strips are held in contact with each other melts a hole of about 1/8th inch in diameter in the strips and leaves them fused together around the periphery of the hole. The spot bonding can also be done by applying a drop of an adhesive to one of the strips and bringing them into contact with each other.

The spot bond may be at a single point on the strips or at several points across the width of the strips or may be a continuous bond extending across the strips. However the bonding is done, the bond must be weaker than the strips 39 themselves.

FIG. 8 shows a condom 50 on a form 51 with a pair of strips 52 positioned on opposite sides of the condom 50 prior to bonding the strips together, with the condom 50 having a reservoir 55 connected to the body of the condom 50 by a generally frustoconical portion 57. It is preferred that the strips 52 be bonded to each other as close to the main body of the condom 50 as is practical. At the same time, it is critical that the reservoir 55 not be damaged by the spot bonding operation.

The form 51 is provided with a rounded end having therein a recess 56 in communication with a passageway 59 which is connectable to a vacuum source 60. The purpose of this structure is to invert the reservoir 55 and get it out of the way of the spot bonding operation. This prevents any damage to the reservoir 55 and allows the spot bonding to be done closer to the main body of the condom while providing the advantages of the inverted reservoir described above.

FIG. 9 shows the structure of FIG. 8 after the reservoir 55 has been inverted and the strips 52 have been bonded to each other. From this it will be seen that the reservoir is well out of the way of the bonding step. Also, the reservoir will retain its inverted configuration and will have the configuration shown in FIG. 6 when it is put on.

The preferred recess 56 is cylindrical in configuration and has a depth sufficiently great to receive the reservoir 55. The diameter of the open end of the recess 56 should be at least as great as the diameter of the reservoir 55 of the condom 50 and is preferably somewhat greater. If the diameter of the open end of the recess 56 is not as great as the diameter of the reservoir 55 the reservoir will not invert when the vacuum is applied but will flatten and remain extended from the end of the form. This will interfere with the spot bonding process and will likely cause the reservoir to be damaged in the process. Also, when the vacuum is released the reservoir will return to the configuration shown in FIG. 8.

The open end of the recess 56 should have a diameter in the range extending from the diameter of the reservoir 55 to about 75% of the diameter of the inflated (but not stretched) condom 50. If the diameter of the open end of the recess 56 goes above about 75% of the condom diameter more of the frustoconical portion 57 will be inverted and there is a greater risk that the end of the inverted reservoir will be caught between the penis and the rolled body portion of the condom as the condom is put on. This would render the reservoir useless.

Preferably, the diameter of the open end of the recess 56 is about 55% to 70% of the diameter of the body of the condom (provided that the smaller diameter is as great as the diameter of the reservoir). With this diameter range, about one half of the frustoconical portion 57 (measured along the axis of the condom) will be inverted with the reservoir to balance the amounts that the reservoir and the frustoconical extend above and below the plane or the rolled condom.

The reservoir 55 easily retains its inverted configuration during further handling and processing even when handled fairly roughly. This is true whether the condom is the conventional type shown in FIG. 1 or the type shown in FIGS. 3–6 (the latter being preferred for the reason that the inverted configuration is the natural configuration of the condom). It is believed that the reservoir's resistance to losing its inverted configuration is the result of the configuration of the reservoir. Significantly more force is required to cause the generally cylindrical reservoir to go from the inverted to the non-inverted state than would be required for a reservoir having some other configuration. For example, if the reservoir had a hemispherical configuration it would be significantly more likely to lose its inverted configuration during further processing. This can be shown by attaching a thread to the tip of the reservoir, inverting the reservoir and part of the frustoconical portion and then, with the condom held level, adding paper clips to the thread.

Applicant has found that the weight of two paper clips is enough weight to make the frustoconical portion lose its inverted configuration but that five or more must be added to cause the generally cylindrical reservoir to lose its inverted configuration. Thus, this generally cylindrical reservoir has over twice the resistance to losing its inverted configuration as does the substantially hemispherical frustoconical portion.

Applicant has found that the use of the strips makes condoms more difficult to roll, with this difficulty increasing as the width and thickness of the strips is increased. When the widths of the strips are increased to the point where premature unrolling of the condom (i.e., a small amount of unrolling as the condom is removed from the package) is prevented, the difficulty of rolling the condom is significantly increased. If the condom fails to roll when a rolling force is applied it will slide along the form on which it is mounted for rolling and form an accordion-like fold adjacent to the open end of the condom. This unacceptable result is prevented by rolling the condom while it is stretched at least 5%, and preferably 10%, in a circumferential direction.

What is claimed is:

1. A condom having an elongated tubular body portion having an open end and a closed end, said closed end having thereon a generally cylindrical reservoir, said reservoir having a proximal end secured to the closed end of the condom and a closed distal free end spaced axially from said proximal end, at least a portion of said reservoir being positioned inside the remainder of the condom with said free end extending in the direction of the open end of the condom.

2. The device of claim 1 wherein the amount of said reservoir which is positioned inside the remainder of the condom is sufficiently great that said closed distal end of the reservoir is axially positioned between the proximal end of the reservoir and the open end of the condom.

3. The device of claim 1 wherein the condom is in a rolled condition and is positioned between a pair of packaging sheets, said sheets being secured to each other around the periphery thereof to form a package for the condom.

4. The device of claim 2 wherein substantially all of the reservoir is inside the condom such that substantially all of the reservoir extends from said proximal end of said reservoir toward the open end of the condom.

5. The device of claim 3 wherein a pair of strips are rolled into the condom on opposite sides thereof, said strips having free ends extending away from each other and being secured to opposite sides of the package.

6. The device of claim 5 wherein the sum of the widths of the strips is at least 20% of the length of the circumference of the rolled condom.

7. The device of claim 5 wherein intermediate portions of the strips are bonded to each other in a bond which has a breaking strength which is lower than the breaking strength of the strips.

8. A contraceptive device, comprising
   a. an elongated condom having an open end and a closed end, said condom being rolled, and
   b. a pair of strips rolled into the condom on opposite sides thereof and having free ends extending away from each other, said strips having intermediate portions which are secured to each other in a bond adjacent to the closed end of the condom, said bond having a strength such that when the free ends of the strips are pulled away from each other under an increasing tension the bond will break before either of the strips breaks.

9. The device of claim 8 wherein the strips are fused to each other to form said bond.

10. The device of claim 8 wherein the condom is positioned between a pair of packaging sheets with the free ends of the strips extending toward opposite edges of the sheets, said sheets being secured to each other around the edges thereof to form a package for the condom.

11. The device of claim 8 wherein the sum of the widths of the strips is at least 20% of the length of the circumference of the rolled condom.

12. The device of claim 8 wherein the combined widths of the strips is sufficient to cause the rolled condom to assume a geneallly elliptical configuration having a length to width ratio of at least 1.2.

13. The device of claim 8 wherein the closed end of the condom is provided with a reservoir, said reservoir being inside the condom and having a free end extending toward the open end of the condom.

14. The device of claim 13 wherein the reservoir has a generally cylindrical configuration.

15. A process for assembling a contraceptive device made up of a pair of strips and a condom having an open end and a closed end having thereon a reservoir, comprising
   a. providing an elongated form having a free end, said free end having therein a recess, said recess having cross sectional dimensions greater than the cross sectional dimensions of the reservoir, b. placing the condom in unrolled condition oil the form, c. placing the strips in contact with the condom on opposite sides thereof with the strips extending along the condom, d. applying a negative pressure to the recess to invert the reservoir of the condom, e. bringing the strips together adjacent to the closed end of the condom, and f. securing the strips to each other in a bond which will break before one of the strips breaks when an increasing tension is applied to the strips.

* * * * *